United States Patent [19]

Heine et al.

[11] 4,363,926
[45] Dec. 14, 1982

[54] PREPARATION OF NOVEL 1-HYDROXYCYCLOPROPANECARBOXYLIC ACID INTERMEDIATES

[75] Inventors: Hans-Georg Heine, Krefeld; Hans-Joachim Knops, Wuppertal; Uwe Priesnitz, Solingen, all of Fed. Rep. of Germany

[73] Assignee: Bayer Aktiengesellschaft, Leverkusen, Fed. Rep. of Germany

[21] Appl. No.: 303,668

[22] Filed: Sep. 18, 1981

[30] Foreign Application Priority Data

Oct. 2, 1980 [DE] Fed. Rep. of Germany ....... 3037302

[51] Int. Cl.$^3$ .............................................. C07F 7/18
[52] U.S. Cl. ................................... 556/442; 562/506; 562/500
[58] Field of Search .................... 556/442; 562/506
[56] References Cited

U.S. PATENT DOCUMENTS 4,293,704 10/1981 Bernady et al. ..................... 556/442

FOREIGN PATENT DOCUMENTS 2128327 12/1972 Fed. Rep. of Germany .
3005358 9/1980 Fed. Rep. of Germany .

OTHER PUBLICATIONS

Chemical Abstracts Band 85, Nr. 1, Jul. 5, 1976.
Chemical Abstracts Band 75, Nr. 15, Oct. 11, 1971.

Primary Examiner—Paul F. Shaver
Attorney, Agent, or Firm—Sprung, Horn, Kramer & Woods

[57] ABSTRACT

A bissilylated 1-hydroxycyclopropanecarboxylic acid of the formula

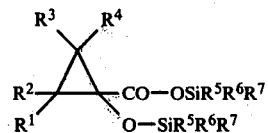

in which
$R^1$, $R^2$, $R^3$ and $R^4$ each independently is a hydrogen atom or an alkyl radical, and additionally $R^2$ and $R^3$ can together form a 3- to 5-membered carbon bridge, and
$R^5$, $R^6$ and $R^7$ each independently is an alkyl radical, is produced by oxidizing with oxygen a cyclobutene-1,2-diol-bis-trialkyl-silyl ether of the formula

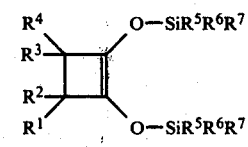

The products, without isolation, may directly be hydrolyzed to remove the silyl radicals and form known intermediates for further reaction.

9 Claims, No Drawings

PREPARATION OF NOVEL 1-HYDROXYCYCLOPROPANECARBOXYLIC ACID INTERMEDIATES

The present invention relates to certain new bis-silylated 1-hydroxycyclopropanecarboxylic acids, which can be used as intermediate products for the synthesis of 1-hydroxycyclopropanecarboxylic acids, and to a process for their preparation.

The present invention now provides, as new compounds, bissilylated 1-hydroxycyclopropanecarboxylic acids of the general formula

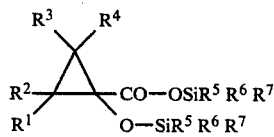

in which
R$^1$, R$^2$, R$^3$ and R$^4$ are identical or different and represent a hydrogen atom or an alkyl radical, and additionally R$^2$ and R$^3$ can also together represent a saturated or unsaturated 3-membered to 5-membered methylene bridge, and
R$^5$, R$^6$ and R$^7$ are identical or different and represent alkyl radicals.

The compounds of the formula (I) according to the present invention can optionally occur as geometrical (cis,trans) and optical isomers; they occur preferably as isomer mixtures.

According to the present invention we further provide a bissilylated 1-hydroxycyclopropanecarboxylic acid of the present invention, characterized in that a cyclobutene-1,2-diol-bis-trialkylsilyl ether of the general formula

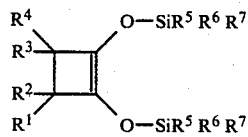

in which R$^1$ to R$^7$ have the meaning given above, is reacted with oxygen as oxidizing agent, if appropriate, in the presence of an inert organic diluent and, if appropriate, in the presence of a catalyst.

Preferred compounds according to the present invention are those in which R$^1$, R$^2$, R$^3$ and R$^4$ are identical or different and represent a hydrogen atom or an alkyl radical with 1 to 4 carbon atoms, and in addition, R$^2$ and R$^3$ can also together represent an optionally unsaturated tetramethylene bridge, and R$^5$, R$^6$ and R$^7$ are identical or different and represent an alkyl radical with 1 to 4 carbon atoms. The following may be mentioned as examples:

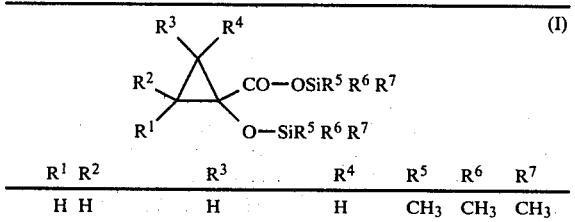

| R$^1$ | R$^2$ | R$^3$ | R$^4$ | R$^5$ | R$^6$ | R$^7$ |
|---|---|---|---|---|---|---|
| H | H | H | H | CH$_3$ | CH$_3$ | CH$_3$ |
| CH$_3$ | CH$_3$ | H | H | CH$_3$ | CH$_3$ | CH$_3$ |
| CH$_3$ | CH$_3$ | CH$_3$ | CH$_3$ | CH$_3$ | CH$_3$ | CH$_3$ |
| CH$_3$ | H | H | H | CH$_3$ | CH$_3$ | CH$_3$ |
| C$_2$H$_5$ | H | H | H | CH$_3$ | CH$_3$ | CH$_3$ |
| i-C$_3$H$_7$ | H | H | H | CH$_3$ | CH$_3$ | CH$_3$ |
| t-C$_4$H$_9$ | H | H | H | CH$_3$ | CH$_3$ | CH$_3$ |
| n-C$_3$H$_7$ | H | H | H | CH$_3$ | CH$_3$ | CH$_3$ |
| n-C$_4$H$_9$ | H | H | H | CH$_3$ | CH$_3$ | CH$_3$ |
| i-C$_4$H$_9$ | H | H | H | CH$_3$ | CH$_3$ | CH$_3$ |
| H | —CH$_2$CH$_2$CH$_2$CH$_2$— | | H | CH$_3$ | CH$_3$ | CH$_3$ |
| H | —CH$_2$—CH=CH—CH$_2$— | | H | CH$_3$ | CH$_3$ | CH$_3$ |

If, for example, cyclobutene-1,2-diol-bis-trimethylsilyl ether and air are employed as starting materials, the course of the reaction according to the present invention is illustrated by the following equation:

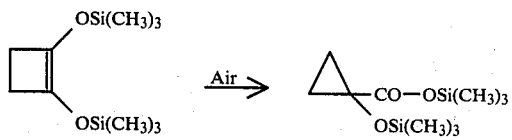

It is surprising that, under the given reaction conditions, both silyl groups are preserved and, with the uptake of formally one oxygen atom, the ring contraction occurs.

Preferred cyclobutene-1,2-diol-bis-trialkylsilyl ethers to be used as starting materials for the process according to the invention are those compounds of the formula (II) in which R$^1$ to R$^7$ represent those radicals which have already been mentioned for these substituents in the description of the preferred compounds according to the present invention.

Cyclobutene-1,2-diol-bis-trialkylsilyl ethers of the formula (II) are known (see, for example, Synthesis 1971, 236 et seq.) and they can be obtained according to the process given in this reference by acyloin condensation of the succinic acid esters in the presence of trialkylsilanes and sodium.

The oxygen to be used as oxidizing agent for the process according to the invention is preferably employed in the form of air. It is also possible to employ oxygen in a singlet state, produced by photoexcitation in the presence of a sensitizer.

The reaction according to the invention is carried out, if appropriate, in the presence of an inert organic diluent. These diluents preferably include aromatic hydrocarbons (such as toluene and xylene), ethers (such as diethyl ether) and chlorinated hydrocarbons (such as chlorobenzene or carbon tetrachloride). However, other inert organic solvents are, in principle, also possible, such as nitriles and esters.

The reaction according to the invention can be carried out, if appropriate, in the presence of a catalyst. Any of the catalysts which are customarily used for the air oxidation process can be employed, such as oxides an salts of transition metals. The reaction can, however, also be carried out in the presence of light.

The reaction temperatures in the reaction according to the invention can be varied within a relatively large range. In general, the temperatures are between 0° and 150° C., preferably between 20° and 120° C.

The compounds of the formula (I) can be isolated in customary manner. However, they can also be directly further converted to the corresponding 1-hydroxycyclopropanecarboxylic acids of the formula

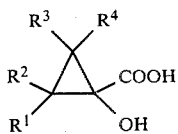
(III)

in which $R^1$ to $R^4$ have the meaning given above, by introducing dry gaseous hydrogen halide, such as, preferably, hydrogen chloride, into the reaction solution. In this reaction, the 1-hydroxycyclopropanecarboxylic acids are formed as crystalline solids, which are filtered off by suction and dried.

The new bissilylated 1-hydroxycyclopropanecarboxylic acids of the formula (I) represent consequently, as already mentioned, interesting intermediate products for the preparation of 1-hydroxycyclopropanecarboxylic acids, which can be obtained in this manner, in a simple one pot reaction, in pure form and in good yields, also on an industrial scale.

The 1-hydroxycyclopropanecarboxylic acids of the formula (III) are largely known (see, for example, Liebigs Ann. Chem. 1976, 463 et seq.). They represent generally interesting intermediate products, in particular also for the synthesis of fungicidally active compounds.

Thus, for example, by reaction with 3,5-dihalogenophenylisocyanates in the presence of an inert organic solvent (such as aromatic hydrocarbons) and, if appropriate, in the presence of a base (such as triethylamine) at a temperature between 20° and 100° C., the fungicidally highly active spiro derivatives of 3-(3,5-dihalogenophenyl)-oxazolidine-2,4-diones of the general formula

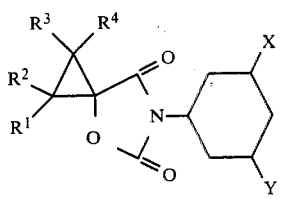
(IV)

in which $R^1$ to $R^4$ have the meaning given above and X and Y represent halogen atoms,
are obtained (see U.S. Pat. No. 4,200,645 and U.S. Ser. No. 095,715 now U.S. Pat. No. 4,267,186).

EXAMPLE 1

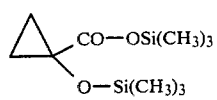

(a) Dried air was introduced into 46.0 g (0.2 mole) of cyclobutene-1,2-diol-bis-trimethylsilyl ether at a bath temperature of 120° C., while stirring. The conversion was monitored by means of NMR spectroscopy. After 6.5 hours, the reaction mixture was allowed to cool and was fractionally distilled in an annular-gap column. 33.7 g (68% of theory) of trimethylsilyl 1-trimethylsiloxycyclopropanecarboxylate with a boiling point of 78° to 80° C./17.5 mbar and with a refractive index of $n_D^{20}=1.422$ were obtained.

(b) Dried air was introduced into 46.0 g (0.2 mole) of cyclobutene-1,2-diol-bis-trimethylsilyl ether at a temperature of 20° C., while stirring, until complete conversion had taken place (72 hours). The slightly yellow coloured reaction product was distilled in an annular-gap colored 32.0 g (66% of theory) of trimethylsilyl 1-trimethylsiloxy-cyclopropanecarboxylate with the boiling point mentioned above were obtained.

(c) Secondary product

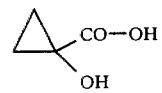

(Preparation starting from cyclobutene-1,2-diol-bis-trimethylsilyl ether as in Example 1 (a) or (b), in which, however, the end product according to Example 1 (a) or (b) was not isolated, but was directly further worked up to give 1-hydroxy-cyclopropanecarboxylic acid according to the above formula).

80 g of 1,2-bis-(trimethylsiloxy)-cyclobut-1-ene were diluted with 250 ml of toluene and air was introduced, while stirring, at 90° C. for 18 to 24 hours. The reaction was monitored for completion by means of gas chromatography. Hydrogen chloride gas was then introduced at room temperature for 2 to 3 hours, the precipitated crystals were filtered off by suction and recrystallized from toluene. 26.7 g (75% of theory relative to the silyl ether employed) of 1-hydroxycyclopropanecarboxylic acid with a melting point of 102° to 105° C. were obtained.

EXAMPLE 2

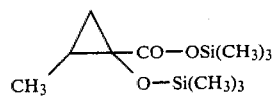

Dried air was introduced into 20.0 g (0.082 mole) of 3-methyl-1,2-bis-(trimethylsiloxy)-cyclobut-1-ene at 100° C., while stirring, until complete conversion had taken place (4 to 6 hours). After cooling down to 50° C., the reaction mixture was fractionally distilled. 14.2 g (67% of theory) of trimethylsilyl 2-methyl-1-trimethylsiloxy-cyclopropanecarboxylate were obtained as a mixture of isomers with a boiling point of 90° to 97° C./17.5 mbar and with a refractive index $n_D^{20}=1.424$.

EXAMPLE 3

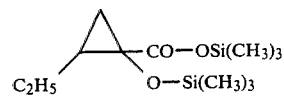

Under the reaction conditions given in Example 2, starting with 3-ethyl-1,2-bis-(trimethylsiloxy)-cyclobut-1-ene, trimethylsilyl 2-ethyl-1-trimethylsiloxy-cyclopropanecarboxylate was obtained in 75% yield as a mixture of isomers with a boiling point of 48° to 57° C./0.4 mbar and with a refractive index $n_D^{20}=1.425$.

EXAMPLE 4

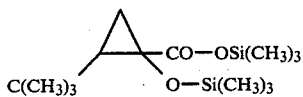

Under the reaction conditions given in Example 2, starting from 3-tert.-butyl-1,2-bis-(trimethylsiloxy)-cyclobut-1-ene, trimethylsilyl 2-tert.-butyl-1-trimethylsiloxy-cyclopropanecarboxylate was obtained in 57% yield (relative to conversion) as a mixture of isomers with a boiling point of 48° to 57° C./0.2 mbar and with a refractive index $n_D^{20}=1.4372$.

EXAMPLE 5

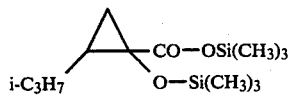

Under the reaction conditions given in Example 2, starting with 3-isopropyl-1,2-bis-(trimethylsiloxy)-cyclobut-1-ene (0.1 mole), trimethylsilyl 2-isopropyl-1-trimethyl°-siloxy-cyclopropanecarboxylate was obtained in 60% yield with a boiling point of 100° to 111° C./13 mbar and with a refractive index $n_D^{20}=1.4282$.

(b) Secondary product

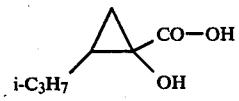

17.0 g (0.06 mole) of trimethylsilyl 2-isopropyl°-1-trimethylsiloxy-cyclopropanecarboxylate were stirred for 2 hours at 30° C. in 100 ml of toluene saturated with hydrogen chloride. Dry nitrogen was then passed through the solution for 1 hour and the precipitate was filtered off. Crystallization from xylene yielded 2-isopropyl-1-hydroxycyclopropanecarboxylic acid (6.1 g) with a melting point of 135° to 138° C.

EXAMPLE 6

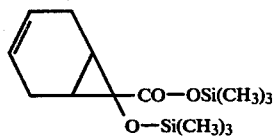

Under the reaction conditions given in Example 2, starting from 7,8-bis-trimethylsiloxy-bicyclo [4,2,0]octa-3,7-diene, trimethylsilyl 7-trimethylsiloxy-bicyclo [4,1,0]hept-3-ene-7-carboxylate was obtained in 54% yield with a boiling point of 71° to 82° C./0.1–1.0 mbar and with a refractive index $n_D^{20}=1.4642$.

It will be appreciated that the instant specification and examples are set forth by way of illustration and not limitation, and that various modifications and changes may be made without departing from the spirit and scope of the present invention.

We claim:

1. A bissilylated 1-hydroxycyclopropanecarboxylic acid of the formula

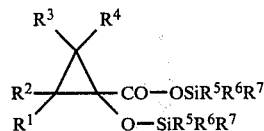

in which
$R^1$, $R^2$, $R^3$ and $R^4$ each independently is a hydrogen atom or an alkyl radical, and additionally $R^2$ and $R^3$ can together form a 3- to 5-membered carbon bridge, and
$R^5$, $R^6$ and $R^7$ each independently is an alkyl radical.

2. A compound according to claim 1, in which
$R^1$, $R^2$, $R^3$ and $R^4$ each independently is a hydrogen atom or an alkyl radical with 1 to 4 carbon atoms, and additionally $R^2$ and $R^3$ can together form an optionally unsaturated tetramethylene bridge, and
$R^5$, $R^6$ and $R^7$ each independently is an alkyl radical with 1 to 4 carbon atoms.

3. A process for the production of a compound according to claim 1, comprising oxidizing with oxygen a cyclobutene-1,2-diol-bis-trialkyl-silyl ether of the formula

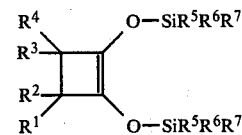

4. A process according to claim 3, wherein the reaction is carried out in the presence of an inert organic diluent.

5. A process according to claim 3, wherein the reaction is carried out in the presence of a catalyst.

6. A process according to claim 3, wherein the oxygen used as the oxidizing agent is employed in the form of air.

7. A process according to claim 3, wherein the reaction is carried out at a temperature between about 0° and 150° C.

8. A process according to claim 4, including the subsequent step of introducing hydrogen chloride gas into the reaction solution thereby directly to hydrolyze the silyl radicals and replace them with hydrogen.

9. A process according to claim 8, wherein the oxygen used as the oxidizing agent is employed in the form of air and the reaction is carried out at a temperature between about 20° and 120° C.

* * * * *